United States Patent [19]

Engel

[11] 4,238,505

[45] Dec. 9, 1980

[54] INSECTICIDAL BIPHENYLMETHYL PERHALOALKYLVINYLCYCLOPROPANECARBOXYLATES

[75] Inventor: John F. Engel, Medina, N.Y.

[73] Assignee: FMC Corporation, Philadelphia, Pa.

[21] Appl. No.: 52,043

[22] Filed: Jun. 25, 1979

Related U.S. Application Data

[63] Continuation of Ser. No. 927,198, Jul. 24, 1978, abandoned, which is a continuation of Ser. No. 870,973, Jan. 20, 1978, abandoned.

[51] Int. Cl.³ .................. A01N 9/24; C07D 69/73
[52] U.S. Cl. .................................. 424/305; 424/306; 560/124
[58] Field of Search ................. 560/124; 424/305, 306

[56] References Cited

U.S. PATENT DOCUMENTS

| 4,130,657 | 12/1978 | Plummer | 424/305 |
| 4,157,447 | 6/1979 | Engel | 560/8 |

FOREIGN PATENT DOCUMENTS

| 858137 | 2/1978 | Belgium . |
| 858163 | 2/1978 | Belgium . |
| 863151 | 7/1978 | Belgium . |
| 52-14749 | 2/1977 | Japan . |

*Primary Examiner*—Richard Raymond
*Attorney, Agent, or Firm*—Robert M. Kennedy; Robert L. Andersen; H. Robinson Ertelt

[57] ABSTRACT

Perhaloalkylvinylcyclopropanecarboxylates having the general formula:

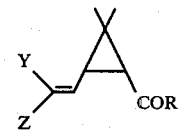

wherein one of Y and Z is a perhaloalkyl group and the other is hydrogen, halogen, or lower alkyl; and R is —OR¹ where R¹ is an optionally substituted biphenylmethyl radical are disclosed. The insecticidal efficacy and preparation of the compounds and their intermediates are described and exemplified.

11 Claims, No Drawings

INSECTICIDAL BIPHENYLMETHYL PERHALOALKYLVINYLCYCLOPROPANECARBOXYLATES

This application is a continuation in part of copending U.S. Ser. No. 927,198, filed July 24, 1978, now abandoned, which is a continuation in part of Ser. No. 870,973, filed Jan. 20, 1978, now abandoned.

The present invention is directed to a novel class of cyclopropanecarboxylate insecticides, and to an insecticidal method and composition. More particularly, the invention is directed to insecticidal biphenylmethyl perhaloalkylvinylcyclopropanecarboxylates set forth in Formula I.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. A noteworthy advance in this area was the discovery by Elliott et al. of certain highly active dihalovinylcyclopropanecarboxylates such as permethrin, the common name for 3-phenoxybenzyl 3-($\beta,\beta$-dichlorovinyl)-2,2-dimethylcyclopropanecarboxylate. This class of compounds set forth in U.S. Pat. No. 4,024,163, issued May 17, 1977, exhibits substantially improved photostability when compared with previously available cyclopropanecarboxylates.

The present invention provides a new class of insecticidal cyclopropanecarboxylates, namely, biphenylmethyl perhaloalkylvinylcyclopropanecarboxylates, exhibiting a remarkable level of insecticidal activity. The present invention also provides novel insecticidal compositions of the foregoing compounds, and a method for controlling insects.

In this application, the term "lower", as applied to an alkyl group means having 1-6 carbon atoms, preferably 1-4 carbon atoms. The term "halo" or "halogen" means bromine, chlorine, or fluorine. With respect to a pherhaloalkyl group the halogens may be the same or different and are suitably selected from fluorine and chlorine with fluorine being preferred. These definitions are applicable throughout the specification and claims except where a contrary meaning is clearly indicated.

The insecticidal compounds of this invention are cyclopropanecarboxylates of the general formula

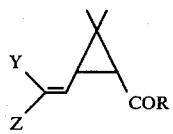

wherein one of Y and Z is a perhaloalkyl group having 1 to 4 carbon atoms, preferably 1 or 2 carbon atoms, and the other is hydrogen, halogen, or lower alkyl.

R is —OR$^1$ where R$^1$ is a group of the formula

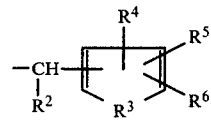

in which R$^2$ is hydrogen, R$^3$ is vinylene; R$^4$ and R$^5$ are independently hydrogen, lower alkyl, halogen, or haloalkyl; and R$^6$ is phenyl which may be substituted with one to three substituents selected from halogen and lower alkyl.

Particularly desirable compounds are cyclopropanecarboxylates of formula I in which one of Y and Z is trihalomethyl, preferably trifluoromethyl, and the other is halogen; R$^2$ is hydrogen; R$^4$ and R$^5$ are independently hydrogen, lower alkyl or halogen; and R$^6$ is phenyl which may be substituted with one to three substituents selected from halogen and lower alkyl. In the alcohol portion of these compounds a desirable placement of R$^4$, R$^5$, and R$^6$ is as shown in the following partial formula:

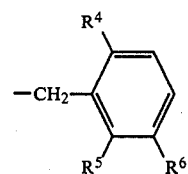

The insecticidal compounds of this invention and certain intermediates therefor exist as cis and trans geometrical isomers, i.e., the carboxy and the substituted vinyl groups at the 1 and 3 positions of the cyclopropane ring are either cis or trans with respect to each other. Preparation of such compounds will usually yield a mixture of cis and trans isomers, designated cis,trans, in which the ratio of cis to trans may vary over a wide range. For purposes of this application the designations cis and trans are assigned in accordance with P. E. Burt, et al., Pestic. Sci., 5 791-799 (1974). The compounds of this invention may also exist as E or Z isomers or as mixtures of E and Z isomers, designated E, Z, depending on the spatial relationship of substituents on the $\alpha$-carbon of the vinyl group to those on the $\beta$-carbon of the vinyl group.

In the cyclopropanecarboxylate art it is known there may be substantial differences in the level of insecticidal activity between the cis and trans isomers. In general, as between the cis and trans isomer of a given cyclopropanecarboxylate, the cis isomer is usually more active than the trans and also more active than the cis,-trans mixture. Similar differences in activity may also occur with respect to the E and Z isomers.

Unless a contrary intent is expressed, the invention embodies and includes all compounds in which the carboxy and substituted vinyl groups at the 1 and 3 positions of the cyclopropane ring are cis or trans, or a mixture of cis and trans configuration with respect to each other. Similarly, the individual E and Z isomers, as well as the mixtures, are also contemplated by and within the scope of the present invention. The enantiomers of these isomers are also included within the scope of the invention.

The compounds may be prepared from alkanoates of the formula

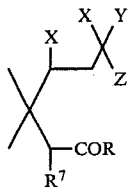

in which Y and Z are defined as above; R is lower alkoxy, such as methoxy or ethoxy, or —OR¹; R⁷ is hydrogen, lower alkylcarbonyl, lower alkoxycarbonyl, or cyano, preferably hydrogen; and X is chloro or bromo. Example 1 illustrates a method for preparation of the alkanoate intermediates of formula II whereby a lower alkyl 3,3-dimethyl-4-pentenoate is allowed to react with a compound of the formula X₂C(Y)(Z) wherein X, Y, and Z are as defined above.

Dehydrohalogenation of the compound of formula II followed, if necessary, by hydrolysis of the ester and, also if necessary, halogenation of the resulting carboxyl group gives a compound of the formula

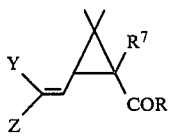

in which R is lower alkoxy, hydroxy, halogen, or —OR¹, and Y, Z and R⁷ are as defined above. The dehydrohalogenation reaction may proceed through one or more intermediates of the formulas:

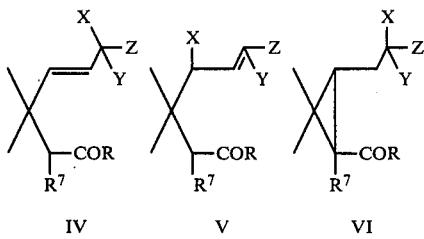

and may be conducted in a single step by removal of 2 equivalents of hydrogen halide, HX, to give a compound of formula III directly or in multiple steps under conditions allowing a sequential removal of the 2 equivalents of HX in separate reactions. These intermediates or mixtures thereof may be recovered if desired. The compound of formula III is then converted to the compound of formula I by methods known to the art, for example, by removing R⁷ (if other than hydrogen) and, where R is lower alkoxy, hydroxy, or halogen, esterifying or transesterifying with HOR¹. Alternatively, where R is hydroxy, the compound of formula III may be converted to the compound of formula I (R=OR¹) by removal of R⁷ followed by reaction with R¹X in which X is a suitable leaving group such as bromine.

The examples which follow illustrate preparation of the insecticidal compounds and intermediates therefor in accordance with the general methods described above. In the examples all temperatures are in degrees centigrade, all pressures are in mm. Hg, and reduced pressure for concentrations of liquid was produced by a water aspirator unless otherwise specified.

Example 1 illustrates the preparation of compounds of formula II.

EXAMPLE 1

SYNTHESIS OF ETHYL 3,3-DIMETHYL-4,6,6-TRICHLORO-7,7,7-TRIFLUOROHEPTANOATE

A stirred solution of 44.6 g (0.267 mole) of ethyl 3,3-dimethyl-4-pentenoate, 100 g (0.533 mole) of 1,1,1-trichlorotrifluoroethane, 0.27 g (0.0027 mole) of cuprous chloride, and 8.2 g (0.134 mole) of ethanolamine in 270 ml of tertiary butyl alcohol, under a nitrogen atmosphere, was heated at reflux for 16 hours. The reaction mixture was cooled to ambient temperature and extracted with three portions of 100 ml each of diethyl ether. A precipitate formed in the extracts, and was removed by vacuum filtration. The filter cake was washed with two portions of 25 ml each of diethyl ether. The ether extracts were combined with the washings, and the whole was concentrated under reduced pressure to an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87°/0.12–0.15 mm. The nmr spectrum was consistent with the assigned structure.

Additional intermediates of formula II, prepared in accordance with the method illustrated in Example 1, are set forth in Table I.

Examples 2 and 3 illustrate preparation of the lower alkyl esters of formula III. Example 2 is a two-step process via the intermediate of formula VI. Example 3 is a one-step process.

EXAMPLE 2

SYNTHESIS OF METHYL CIS,TRANS-3-(2-CHLORO-3,3,3-TRIFLUORO-1-PROPENYL)-2,2-DIMETHYLCYCLO-PROPANECARBOXYLATE

A. Preparation of methyl cis,trans-3-(2,2-dichloro-3,3,3-trifluoropropyl)-2,2-dimethylcyclopropanecarboxylate as an intermediate A stirred solution of 37.0 g (0.112 mole) of methyl 3,3-dimethyl-4,6,6-trichloro-7,7,7-trifluoroheptanoate, 50 ml of tert-butyl alcohol, 50 ml of dimethylformamide, and 50 ml of hexane, under an argon atmosphere, was cooled to −5° C. To the stirred solution was added dropwise a solution of 16.4 g (0.14 mole) of potassium tert-butoxide in 200 ml of tert-butyl alcohol at such a rate so as to maintain the reaction mixture temperature at −3° to −5° C. Upon complete addition, the reaction mixture was stirred for 4 hours at −3° to −5° C., then poured into a solution of 8.0 g of ammonium chloride in 250 ml of water. The mixture was extracted with two portions of 200 ml each of diethyl ether. The combined ether extracts were washed with two portions of 200 ml each of water. The ether layer was dried with sodium sulfate and filtered. The filtrate was evaporated under reduced pressure to a residual oil. The oil was distilled under reduced pressure to give 19.8 g of methyl cis,trans-3-(2,2-dichloro-3,3,3-trifluoropropyl)-2,2-dimethylcyclopropanecarboxylate; b.p. 55°–57° C./0.09 mm. The ir and the nmr spectra were consistent with the proposed structure.

Analysis calc'd for $C_{10}H_{13}Cl_2F_3O_2$: C40.98, H4.47; Found: C41.50, H4.41.

B. Synthesis of methyl cis,trans-3-(2-chloro-3,3,3-trifluoro-1-propenyl)-2,2-dimethylcyclopropanecarboxylate.

A stirred solution of 30.6 g (0.105 mole) of methyl cis,trans-3-(2,2-dichloro-3,3,3-trifluoropropyl)-2,2-dimethylcyclopropanecarboxylate and 17.6 g (0.116 mole) of 1,5-diazabicyclo[5.4.0]undec-5-ene in 100 ml of dimethylformamide was heated at 100° C. for 4 hours. The reaction mixture was cooled and poured into a solution of 37.2 ml of concentrated hydrochloric acid in 300 ml of water. The mixture was extracted with three portions of 200 ml each of diethyl ether. The combined ether extracts were washed with an aqueous saturated solution of sodium chloride. The ether layer was dried with sodium sulfate and filtered. The filtrate was evaporated under reduced pressure to give a residual oil. The oil was dissolved in hexane, treated with decolorizing carbon, and filtered. The filtrate was evaporated under reduced pressure to a residual oil. The oil was distilled under reduced pressure to give in three fractions 10.0 g of methyl cis,trans 3-(2-chloro-3,3,3-trifluoro-1-propenyl)-2,2-dimethylcyclopropanecarboxylate; b.p. 40°–60° C./0.05 mm. The ir and the nmr spectra were consistent with the proposed structure. The nmr spectra indicated an 88:12 mixture of cis:trans isomers.

Analysis calc'd for $C_{10}H_{12}ClF_3O_2$: C 46.80; H 4.71; Found: C 46.91; H 4.79.

EXAMPLE 3

SYNTHESIS OF ETHYL CIS,TRANS-3-(2-CHLORO-3,3,3-TRIFLUORO-1-PROPENYL)-2,2-DIMETHYLCYCLOPROPANECARBOXYLATE

To a stirred solution of 78.3 g (0.228 mole) of ethyl 3,3-dimethyl-4,6,6-trichloro-7,7,7-trifluoroheptanoate in 200 ml of distilled ethanol was added dropwise at ambient temperature 500 ml of an ethanolic solution of sodium ethoxide prepared from 11.5 g of metallic sodium (0.50 mole). After complete addition, the reaction mixture was stirred for one hour at ambient temperature, then allowed to stand for 18 hours. The cloudy reaction mixture was filtered and the filtrate evaporated under reduced pressure to give a residue. The residue was slurried in 200 ml of water, and the mixture was extracted with three portions of 50 ml each of diethyl ether. The combined extracts were dried with sodium sulfate and filtered. The filtrate was evaporated under reduced pressure to give, as a residual oil, 58.5 g of ethyl cis,trans-3-(2-chloro-3,3,3-trifluoro-1-propenyl)-2,2-dimethylcyclopropanecarboxylate. The nmr and the ir spectra were consistent with the assigned structure and indicated the product was a mixture of approximately equal parts of cis and trans isomers.

Additional intermediates of formula VI, prepared in accordance with the method illustrated in Example 2A, are set forth in Table II.

Additional lower alkyl esters of formula III, prepared in accordance with Example 2 or Example 3 above, are set forth as Compounds 3.1 to 3.8 of Table III. Compounds 3.1 through 3.7 were prepared in accordance with Example 2. Compound 3.8 was prepared in accordance with Example 3.

EXAMPLE 4

SYNTHESIS OF TRANS AND CIS,TRANS-3-(2-CHLORO-3,3,3-TRIFLUORO-1-PROPENYL)-2,2-DIMETHYLCYCLOPROPANECARBOXYLIC ACID

A solution of 16.2 g (0.06 mole) of ethyl cis,trans-3-(2-chloro-3,3,3-trifluoro-1-propenyl)-2,2-dimethylcyclopropanecarboxylate, prepared in accordance with Example 3, in 94 ml (0.078 mole) of a stock solution containing 3.34 g of sodium hydroxide, 94 ml of ethanol and 6 ml of water was stirred while heating under reflux for a period of 18 hours. The reaction mixture was concentrated under reduced pressure, 25 ml of water was added, and the mixture was acidified to pH 1 using 6 N hydrochloric acid. The acidified mixture was extracted with two portions of 50 ml each of diethyl ether. The combined extracts were dried with magnesium sulfate and filtered. The filtrate was evaporated under reduced pressure to give a residue. The residue was heated with 50 ml of hexane. The hot hexane was decanted from a tarry residue and cooled to yield a solid precipitate, which was collected by filtration, then dried to give 3.3 g of solid, m.p. 97°–103° C. Concentration of the mother liquor provided a second fraction of solid weighing 0.8 g, m.p. 96°–103° C. Nmr spectra of the two fractions indicated the solids were each trans-3-(2-chloro-3,3,3-trifluoro-1-propenyl)-2,2-dimethylcyclopropanecarboxylic acid. The mother liquor was evaporated to a residue. The residue was taken up in 50 ml of hexane and the solution cooled in a freezer for 18 hours. A solid precipitate was collected by filtration and dried to give 4.3 g of a solid, m.p. 64°–74° C. An nmr spectrum indicated the solid was a 50/50 mixture of cis and trans isomers of 3-(2-chloro-3,3,3-trifluoro-1-propenyl)-2,2-dimethylcyclopropanecarboxylic acid.

EXAMPLE 5

SYNTHESIS OF CIS-3-(2-CHLORO-3,3,3-TRIFLUORO-1-PROPENYL)-2,2-DIMETHYLCYCLOPROPANECARBOXYLIC ACID

A stirred solution of 90.0 g (0.35 mole) of methyl cis,trans-3-(2-chloro-3,3,3-trifluoro-1-propenyl)-2,2-dimethylcyclopropanecarboxylate (approximately 90% cis, prepared in accordance with Example 2B), 5.4 ml of concentrated sulfuric acid and 13.8 ml of water in 138 ml of acetic acid was heated under reflux for 1 hour. The reaction mixture was cooled and extracted with two portions of 100 ml each of diethyl ether. The combined extracts were dried with sodium sulfate, filtered, and the filtrate concentrated under reduced pressure to a solid residue. The residue was digested with 300 ml of hexane and the hexane solution was decanted from a dark, tarry residue and allowed to cool to ambient temperature. A solid precipitate formed and was collected by filtration to give 42.4 g of cis-3-(2-chloro-3,3,3-trifluoro-1-propenyl)-2,2-dimethylcyclopropanecarboxylic acid, as determined by NMR spectroscopy. A melting point was not determined. The melting point of another sample of cis acid prepared at a different time was 108°–110° C. The filtrate was concentrated and cooled to give 5.1 g of solid, identified by NMR spectroscopy to be a 50:50 mixture of cis,trans-3-(2-chloro-3,3,3-trifluoro-1-propenyl)-2,2-dimethylcyclopropanecarboxylic acid. The filtrate was cooled in dry ice to give an additional 8.1 g of a 50:50 mixture of the cis,trans isomers.

Additional free acids of formula III, prepared in accordance with Example 4 or Example 5, are set forth as Examples 4.1 through 4.8 of Table III.

EXAMPLE 6

SYNTHESIS OF TRANS-3-(2-CHLORO-3,3,3-TRIFLUORO-1-PROPENYL)-2,2-DIMETHYLCYCLO-PROPANECARBONYL CHLORIDE

To a stirred solution of 4.1 g (0.0173 mole) of trans-3-(2-chloro-3,3,3-trifluoro-1-propenyl)-2,2-dimethylcyclopropanecarboxylic acid in 40 ml of toluene at ambient temperature was added 1.7 g (0.022 mole) of pyridine, then 2.6 g (0.022 mole) of thionyl chloride in 25 ml of toluene. Upon complete addition the reaction mixture was stirred at ambient temperature for 17 hours. The reaction mixture was filtered through diatomaceous earth, and the filtrate was evaporated under reduced pressure to give 3.8 g of trans-3-(2-chloro-3,3,3-trifluoro-1-propenyl)-2,2-dimethylcyclopropanecarbonyl chloride. The ir spectrum was consistent with the assigned structure.

EXAMPLE 7

SYNTHESIS OF CIS-3-(2-CHLORO-3,3,3-TRIFLUORO-1-PROPENYL)-2,2-DIMETHYLCYCLO-PROPANECARBONYL CHLORIDE

A stirred solution of 10.0 g (0.04 mole) of cis-3-(2-chloro-3,3,3-trifluoro-1-propenyl)-2,2-dimethylcyclopropanecarboxylic acid in 100 ml of toluene was heated to 80° C. To this solution at 80° C. was added dropwise over 10 minutes a solution of 10.5 g (0.08 mole) of oxalyl chloride in 5 ml of toluene, and the whole heated at 80° C. for 26 hours. The toluene and excess oxalyl chloride were removed by distillation to give a residual oil which was distilled under reduced pressure using a Kugelrohr bulb to bulb distilling system to give 8.2 g of cis-3-(2-chloro-3,3,3-trifluoro-1-propenyl)-2,2-dimethylcyclopropanecarbonyl chloride; b.p. 85° C./0.09 mm. The nmr and ir spectra were consistent with the proposed structure.

Additional acid chlorides of Formula III, prepared in accordance with Example 6 or Example 7, are set forth as Examples 6.1 through 6.8 in Table III.

Examples 8 through 23 demonstrate the preparation of compounds of formula I in which R is —OR$^1$. The compounds of these examples are shown in Table IV below.

EXAMPLE 8

SYNTHESIS OF [1,1'-BIPHENYL]-3-YLMETHYL CIS-3-(2-CHLORO-3,3,3-TRIFLUORO-1-PROPENYL)-2,2-DIMETHYLCYCLO-PROPANECARBOXYLATE

To a solution of 32.5 g (0.58 mole) of potassium hydroxide in 200 ml of water was added 112 g (0.46 mole) of cis-3-(2-chloro-3,3,3-trifluoro-1-propenyl)-2,2-dimethylcyclopropanecarboxylic acid. To the resulting solution was added 1000 ml of heptane. This mixture was heated at reflux until 200 ml of water was collected in a Dean-Stark trap.

The reaction mixture was cooled to 50° C. and 113.6 g (0.46 mole) of 3-bromomethyl[1,1'-biphenyl] and 1000 ml of acetonitrile were added. 3-Bromomethyl[1,1'-biphenyl] may be prepared according to the method disclosed in U.S. Pat. No. 4,130,657. The resulting mixture was refluxed for 16 hours at which time 4.5 g (0.04 mole) of 1,4-diazabicyclo[2,2,2]octane was added. Refluxing was continued for an additional 4 hours, then the reaction mixture was cooled to room temperature and 600 ml of water was added. The aqueous layer was separated and was washed once with heptane. The heptane wash and the organic layer were combined, washed once with water, dried over anhydrous sodium sulfate, filtered, and the filtrate concentrated under reduced pressure to give 198 g of residual oil.

The residual oil was passed through a 1200 g column of silica gel using successively 4000 ml of hexane, 2000 ml of hexane/diethyl ether (1/1), 1000 ml of hexane/diethyl ether ($\frac{1}{2}$) and finally diethyl ether to elute the product. The appropriate fractions were combined and stripped of solvent to give 113.2 g of semi-pure product which was passed through a second 1200 g silica gel column. The product was eluted successively with 3500 ml of hexane, 2400 ml of hexane/diethyl ether (7/1), and 1800 ml of hexane/diethyl ether (5/1), the appropriate fractions were combined to yield 82.9 g of [1,1'-biphenyl]-3-ylmethyl cis-3-(2-chloro-3,3,3-trifluoro-1-propenyl)-2,2-dimethylcyclopropanecarboxylate as an orange oil. Analysis by liquid chromatography indicated a purity of 93% and a cis/trans isomer ratio of 98/2. The nmr and ir spectra were consistent with the proposed structure.

No boiling point determination was made on this sample, but the boiling point of another sample was 117°–123° C./0.05 mm. Elemental analysis was also done on this other sample.

Analysis calc'd for $C_{22}H_{20}ClF_3O_2$: C 64.63, H 4.92; Found: C 64.70, H 4.97.

EXAMPLE 9

SYNTHESIS OF [1,1'-BIPHENYL]-3-YLMETHYL CIS-3-(2-CHLORO-3,3,4,4,4-PENTAFLUORO-1-BUTENYL)-2,2-DIMETHYLCYCLO-PROPANECARBOXYLATE cis,trans-3-(2-Chloro-3,3,4,4,4-pentafluoro-1-butenyl)-2,2-dimethylcyclopropanecarboxylic acid (4.6 g, 0.015 mole), compound 4.7 in Table III, was converted to its potassium salt by treatment with aqueous 5 N potassium hydroxide solution followed by removal of the water under high vacuum.

A mixture of 0.015 mole of potassium cis,trans-3-(2-chloro-3,3,4,4,4-pentafluoro-1-butenyl)-2,2-dimethylcyclopropanecarboxylate, 32 ml of heptane, 32 ml of acetonitrile, 0.2 g of 1,4-diazabicyclo[2.2.2]octane, and 3.8 g (0.015 mole) of 3-bromomethyl[1,1'-biphenyl] was heated under reflux with stirring for 16 hours. The reaction mixture was allowed to cool, water (100 ml) was added, and the whole extracted twice with heptane. The heptane extracts were combined, dried, filtered, and concentrated to give 6.24 g of crude product.

The crude product was subjected to column chromatography on silica gel, eluting with hexane, hexane-ether mixtures, then ether. Appropriate fractions, determined by thin layer chromatography, were combined and concentrated to give 4.2 g of product which was further purified by chromatography on silica gel, eluting with hexane then hexane-methylene chloride mixtures. Appropriate fractions, determined by thin layer chromatography and nmr analysis, were combined and concentrated to give [1,1'-biphenyl]-3-ylmethyl cis-3-(2- chloro-3,3,4,4,4-pentafluoro-1-butenyl)-2,2-dimethylcyclopropanecarboxylate. The nmr spectrum was consistent with the proposed structure.

Analysis calc'd for $C_{23}H_{20}ClF_4O_2$: C 60.20, H 4.39; Found: C 60.20, H 4.05.

EXAMPLE 10

SYNTHESIS OF [1,1'-BIPHENYL]-3-YLMETHYL TRANS- AND CIS,TRANS 3-(2-CHLORO-3,3,4,4,4-PENTAFLUORO-1-BUTENYL)-2,2-DIMETHYLCYCLOPROPANECARBOXYLATE

Potassium hydroxide (2.0 g, 0.035 mole) was added to a solution of 10.2 g (0.035 mole) of cis,trans-3-(2-chloro-3,3,4,4,4-pentafluoro-1-butenyl)-2,2-dimethylcyclopropanecarboxylic acid in a minimum amount of methanol, and the mixture was stirred until dissolution of the potassium hydroxide, then concentrated under reduced pressure to a solid residue.

The solid residue was dissolved in 125 ml of acetonitrile, and 11.4 g (0.035 mole) of 3-bromomethyl-[1,1'-biphenyl] and 0.2 g of 1,4-diazabicyclo[2,2,2]octane were added and the whole stirred for 16 hours under reflux.

The reaction mixture was allowed to cool, mixed with 100 ml of water, then extracted twice with heptane. The heptane extracts were combined, dried, filtered, and concentrated to give an oily residue.

The oily residue was subjected to column chromatography on silica gel, eluting with hexane, hexanemethylene chloride gradient mixtures, and, finally, methylene chloride.

Nuclear magnetic resonance spectroscopic monitoring of the collected fractions indicated that early fractions contained cis,trans mixtures, and later fractions contained trans product.

Appropriate fractions were combined to give 0.4 g of [1,1'-biphenyl]-3-ylmethyl cis,trans-3-(2-chloro-3,3,4,4,4-pentafluoro-1-butenyl)-2,2-dimethylcyclopropanecarboxylate and 1.1 g of [1,1'-biphenyl]-3-ylmethyl trans-3-[2-chloro-3,3,4,4,4-pentafluoro-1-butenyl]-2,2-dimethylcyclopropanecarboxylate.

Analysis (cis,trans) for $C_{23}H_{20}ClF_5O$: Calc'd: C 60.20, H 4.39; Found: C 60.02, H 4.68.

Analysis (trans) for $C_{23}H_{20}ClF_5O$: Calc'd: C 60.20, H 4.39; Found: C 60.45, H 4.67.

EXAMPLE 11

SYNTHESIS OF [1,1'-BIPHENYL]-3-YLMETHYL CIS- AND TRANS-3-(3-CHLORO-2,3,3-TRIFLUORO-1-PROPENYL)-2,2-DIMETHYLCYCLOPROPANECARBOXYLATE

This compound was prepared in the manner set forth in Examples 8, 9, and 10 above, using 5.0 g (0.021 mole) of cis,trans-3-(3-chloro-2,3,3-trifluoro-1-propenyl)-2,2-dimethylcyclopropanecarboxylic acid (compound 4.8, Table III), 5.1 g (0.021 mole) of 3-bromomethyl[1,1'-biphenyl], 1.2 g (0.021 mole) of potassium hydroxide, and 0.5 g of 1,4,7,10,13,16-hexaoxacyclooctadecane in 50 ml of acetonitrile.

The reaction mixture was heated at reflux for 1 hour, cooled, and poured into 150 ml of water. The mixture was extracted with 3×100 ml of methylene chloride, and the extracts were combined, washed with 100 ml of a saturated aqueous solution of sodium chloride, dried over magnesium sulfate, filtered, and concentrated to give 8.5 g of an amber colored oil.

The amber oil was subjected to high pressure liquid chromatography using 5% ethyl acetate in hexane. Appropriate fractions, determined by thin layer chromatography, were combined and concentrated to give 6.3 g of an amber colored oil. Rechromatography (high pressure, liquid) using 5% ethyl acetate in hexane afforded 2.4 g of cis product and 2.3 g of trans product, as determined by nmr analysis. Kugelrohr bulb to bulb distillation of the individual cis and trans products gave 2.2 g of [1,1'-biphenyl]-3-ylmethyl cis-3-(3-chloro-2,3,3-trifluoro-1-propenyl)-2,2-dimethylcyclopropanecarboxylate, bp 110°/0.1 mm, and 1.7 g of [1,1'-biphenyl]-3-ylmethyl trans-3-(3-chloro-2,3,3-trifluoro-1-propenyl)-2,2-dimethylcyclopropanecarboxylate, bp 112°/0.025 mm.

Analysis (cis) for $C_{22}H_{20}ClF_3O_2$: Calc'd: C 64.63, H 4.93; Found: C 64.60, H 5.00.

Analysis (trans) for $C_{22}H_{20}ClF_3O_2$: Calc'd: C 64.63, H 4.93; Found: C 64.48, H 5.06.

EXAMPLE 12

SYNTHESIS OF [1,1'-BIPHENYL]-3-YLMETHYL CIS- AND TRANS-3-(2,3-DICHLORO-3,3-DIFLUORO-1-PROPENYL)-2,2-DIMETHYLCYCLOPROPANECARBOXYLATE

This compound was prepared in the manner set forth in Examples 8, 9, and 10 above, using 10.8 g (0.036 mole) of pre-prepared potassium salt of cis,trans-3-(2,3-dichloro-3,3-difluoro-1-propenyl)-2,2-dimethylcyclopropanecarboxylic acid (free acid is compound 4.4, Table III), 9.0 g (0.036 mole) of 3-bromomethyl[1,1'-biphenyl], and 1.0 g of 1,4,7,10,13,16—hexaoxacyclooctadecane in 75 ml of acetonitrile.

The reaction mixture was heated at reflux for 3¼ hour, cooled, filtered, and concentrated to give an oil. The oil was dissolved in ether, washed with three 50 ml portions of water, dried, and concentrated to give 15.0 g of an orange colored oil.

The oil was subjected in successive steps to high pressure liquid chromatography (5% ethyl acetate in hexane, yield 8.02 g), Kugelrohr bulb to bulb distillation (yield 3.8 g), column chromatography (silica gel, 5% ethyl acetate in hexane eluant), and, finally, high pressure liquid chromatography (3% ethyl acetate in hexane). Appropriate fractions were combined to give 0.2 g of [1,1'-biphenyl]-3-ylmethyl cis-3-(2,3-dichloro-3,3-difluoro-1-propenyl)-2,2-dimethylcyclopropanecarboxylate and 0.6 g of [1,1'-biphenyl]-3-yl-methyl trans-3-(2,3-dichloro-3,3-difluoro-1-propenyl)-2,2-dimethylcyclopropanecarboxylate. The nmr spectra were consistent with the proposed structures.

Analysis (cis) for $C_{22}H_{20}Cl_2F_2O_2$: Calc'd: C 62.13, H 4.74; Found: C 65.06, H 5.07.

Analysis (trans) for $C_{22}H_{20}Cl_2F_2O_2$: Calc'd: C 62.13, H 4.74; Found: C 62.55, H 4.86.

EXAMPLE 13

SYNTHESIS OF [1,1'-BIPHENYL]-3-YLMETHYL CIS-3-(2-BROMO-3,3,3-TRIFLUORO-1-PROPENYL)-2,2-DIMETHYLCYCLOPROPANECARBOXYLATE

A stirred solution of 0.50 g (0.0027 mole) of [1,1'-biphenyl]-3-ylmethanol, prepared by the method of U.S. Pat. No. 4,130,657, and 0.25 g (0.003 mole) of pyridine in 10 ml of toluene was cooled to 5°–10° C. To this solution was added dropwise a solution of 0.73 g (0.0024 mole) of cis,trans-3-(2-bromo-3,3,3-trifluoro-1-propenyl)-2,2-dimethylcyclopropanecarbonyl chloride (compound 6.1, Table III) in 5 ml of toluene. Upon complete addition the reaction mixture was allowed to warm to ambient temperature and was stirred for 16 hours. The reaction mixture was filtered and the filtrate concentrated under reduced pressure to a residual oil.

The oil was subjected to column chromatography on silica gel, eluting with hexane, hexane-toluene mixtures, then toluene. The appropriate fractions, as determined by nmr analysis and gas phase chromatography, were combined and concentrated to give 0.33 g of [1,1'-biphenyl]-3-ylmethyl cis-3-(2-bromo-3,3,3-trifluoro-1-propenyl)-2,2-dimethylcyclopropanecarboxylate. The nmr and ir spectra were consistent with the proposed structure.

Analysis calc'd for $C_{22}H_{20}BrF_3O_2$: C 58.29; H 4.45; Found: C 57.99; H 4.41.

EXAMPLE 14

SYNTHESIS OF [1,1'-BIPHENYL]-3-YLMETHYL CIS,TRANS-3-(2-BROMO-3,3,3-TRIFLUORO-1-PROPENYL)-2,2-DIMETHYLCYCLOPROPANECARBOXYLATE

A stirred solution of 1.9 g (0.007 mole) of cis,trans-3-(2-bromo-3,3,3-trifluoropropenyl)-2,2-dimethylcyclopropanecarboxylic acid (compound 4.1, Table III) and 2.4 g (0.020 mole) of thionyl chloride was heated at 40°–50° C. for 2.5 hours under a nitrogen atmosphere. The reaction mixture was cooled slightly and concentrated under reduced pressure to give cis,trans-3-(2-bromo-3,3,3-trifluoro-1-propenyl)-2,2-dimethylcyclopropanecarbonyl chloride.

The acid chloride was dissolved in 15 ml of toluene, and the solution was added portionwise at 5'C to a solution of 1.4 g (0.007 mole) of [1,1'-biphenyl]-3-ylmethanol and 0.7 g (0.009 mole) of pyridine in 20 ml of toluene. Upon complete addition, the reaction mixture was stirred with external cooling for about 10 minutes, then the cooling bath was removed and stirring was continued for about 64 hours. The reaction mixture was filtered and the filtrate concentrated to give a yellow colored oil. Gas phase chromatographic analysis indicated the reaction had not gone to completion. The oil was dissolved in 30 ml of toluene, 0.7 g of pyridine added, and the mixture stirred at ambient temperature for 1.5 hours. The mixture was filtered and concentrated to give a yellow colored oil which was subjected to distillation at 110°–135° C./0.05-0.055 mm using a Kugelrohr bulb to bulb distilling system. Appropriate fractions, as determined by thin layer and gas phase chromatographic analysis, were combined to give 1.35 g of an oil. The oil was chromatographed on a silica gel column, eluting with toluene-hexane mixtures to give 0.55 g of [1,1'-biphenyl]-3-ylmethyl cis,trans-3-(2-bromo-3,3,3-trifluoro-1-propenyl)-2,2-dimethylcyclopropanecarboxylate. The nmr spectrum was consistent with the proposed structure.

Analysis calc'd for $C_{22}H_{20}BrF_3O_2$: C 58.29, H 4.45; Found: C 58.42; H 4.67.

EXAMPLE 15

SYNTHESIS OF [1,1'-BIPHENYL]-3-YLMETHYL CIS- AND CIS, TRANS-3-(2,4-DICHLORO-3,3,4,4-TETRAFLUORO-1-BUTENYL)-2,2-DIMETHYLCYCLOPROPANECARBOXYLATE

A solution of 1.5 g (0.005 mole) of cis,trans-3-(2,4-dichloro-3,3,4,4-tetrafluoro-1-butenyl)-2,2-dimethylcyclopropanecarboxylic acid (compound 4.6 in Table III) in 10 ml of methylene chloride was stirred as 3.2 g (0.005 mole) of 40% aqueous tetrabutylammonium hydroxide was added. Upon complete addition the reaction mixture was stirred at ambient temperature for 1.5 hours. The aqueous-organic mixture was dried with sodium sulfate and filtered. The filtrate was concentrated under reduced pressure to give a viscous yellow colored oil. The oil was dissolved in 5 ml of dry dimethylformamide, and 1.0 g (0.004 mole) of 3-bromomethyl[1,1'-biphenyl] was added. Upon complete addition the reaction mixture was stirred at ambient temperature for 16 hours under a dry atmosphere. The reaction mixture was diluted with 25 ml of water and extracted with three portions of hexane. The combined extracts were washed with four portions of water then dried with sodium sulfate, filtered, and the filtrate concentrated under reduced pressure to give 1.9 g of crude product as a clear yellow oil.

A second run of the same reaction using 1.5 g (0.005 mole) of cis,trans-3-(2,4-dichloro-3,3,4,4-tetrafluoro-1-butenyl)-2,2-dimethylcyclopropanecarboxylic acid, 3.2 g (0.005 mole) of 40% aqueous tetrabutylammonium hydroxide, and 1.0 g (0.004 mole) of 3-bromomethyl[1,1'-biphenyl] gave an additional 1.9 g of crude product.

The two batches of crude product were combined and subjected to high pressure liquid chromatography using a 20:1 hexane:ethylacetate mixture as eluant to give 0.8 g of [1,1'-biphenyl]-3-ylmethyl cis,trans-3-(2,4-dichloro-3,3,4,4-tetrafluoro-1-butenyl)-2,2-dimethylcyclopropanecarboxylate. The nmr spectrum, which was consistent with the proposed structure, indicated the cis:trans ratio to be about 80:20.

A separate fraction (1.2 g, cis,trans mixture) from the above liquid chromatography was resubjected to liquid chromatography, using 50:1 hexane:ethyl acetate as an eluant. The appropriate fractions were combined to give 0.8 g of [1,1'-biphenyl]-3-ylmethyl cis-3-(2,4-dichloro-3,3,4,4-tetrafluoro-1-butenyl)-2,2-dimethylcyclopropanecarboxylate. The nmr and ir spectra were consistent with the proposed structure.

Analysis (cis,trans) for $C_{23}H_{20}Cl_2F_4O_2$: Calc'd: C 58.12, H 4.24; Found: C 57.88, H 4.34.

EXAMPLE 16

SYNTHESIS OF [1,1'-BIPHENYL]-3-YLMETHYL CIS- AND CIS, TRANS-3-(3,3,3-TRIFLUORO-1-PROPENYL)-2,2-DIMETHYLCYCLOPROPANECARBOXYLATE

This compound was prepared in the manner of Example 15, using 3.0 g (0.014 mole) of cis,trans-3-(3,3,3-trifluoro-1-propenyl)-2,2-dimethylcyclopropanecarboxylic acid (compound 4.3, Table III), 3.6 g (0.014 mole) of 3-bromomethyl[1,1'-biphenyl] and 9.4 g (0.014 mole) of 40% aqueous tetrabutylammonium hydroxide in 5 ml of methylene chloride and 10 ml of dimethylformamide.

Medium pressure liquid chromatography of the crude product, using 0.5% ethyl acetate in hexane as eluant, gave 3.1 g of a clear oil. The 3.1 g of oil was subjected twice to liquid chromatography, using 2% ethyl acetate in hexane as eluant each time. Combination of appropriate fractions from each chromatography afforded 1.2 g of [1,1'-biphenyl]-3-ylmethyl cis-3-(3,3,3-trifluoro-1-propenyl)-2,2-dimethylcyclopropanecarboxylate and an undetermined amount of [1,1'-biphenyl]-3-ylmethyl cis,trans-3-(3,3,3-trifluoro-1-propenyl)-2,2-dimethylcyclopropanecarboxylate. The nmr and ir spectra were consistent with the proposed structures.

Analysis (cis) for $C_{22}H_{21}F_3O_2$: Calc'd: C 70.57, H 5.67; Found: C 70.65, H 5.66.

Analysis (cis,trans) for $C_{22}H_{21}F_3O_2$: Calc'd: C 70.57, H 5.65; Found: C 70.80, H 5.90.

EXAMPLE 17

SYNTHESIS OF [1,1'-BIPHENYL]-3-YLMETHYL CIS- AND TRANS-3-(2,3,3,3-TETRAFLUORO-1-PROPENYL)-2,2-DIMETHYLCYCLO-PROPANECARBOXYLATE

This compound was prepared in the manner of Example 15, using 1.4 g (0.006 mole) of cis,trans-3-(2,3,3,3-tetrafluoro-1-propenyl)-2,2-dimethylcyclopropanecarboxylic acid (compound 4.2, Table III), 1.5 g (0.006 mole) of 3-bromomethyl[1,1'-biphenyl] and 1.6 g (0.006 mole) of 40% aqueous tetrabutylammonium hydroxide in 15 ml of methylene chloride and 10 ml of dimethylformamide.

The reaction mixture was diluted with water and extracted with 3×100 ml portions of hexane. The hexane extracts were combined, dried over magnesium sulfate, filtered and the filtrate was concentrated under reduced pressure to give 2.5 g of an oil residue. The cis and trans isomers were separated by medium pressure liquid chromatography eluting with 1% ethyl acetate in hexane. The appropriate fractions were combined to give 0.7 g of [1,1'-biphenyl]-3-ylmethyl cis-3-(2,3,3,3-tetrafluoro-1-propenyl)-2,2-dimethylcyclopropanecarboxylate, and 0.2 g of [1,1'-biphenyl]-3-ylmethyl trans-3-(2,3,3,3-tetrafluoro-1-propenyl)-2,2-dimethylcyclopropanecarboxylate. The nmr and ir spectra were consistent with the proposed structures.

Analysis (cis) for $C_{22}H_{20}F_4O_2$: Calc'd: C 67.33, H 5.14; Found: C 67.14, H 5.16. Analysis (trans) for $C_{22}H_{20}F_4O_2$: Calc'd: C 67.33, H 5.14; Found: C 67.28, H 5.26.

EXAMPLE 18

SYNTHESIS OF [1,1'-BIPHENYL]-3-YLMETHYL TRANS-3-(2-BROMO-3,3,3-TRIFLUORO-1-PROPENYL)-2,2-DIMETHYLCYCLO-PROPANECARBOXYLATE

This compound was prepared in the manner of Examples 8, 9, and 10 using 2.0 g (0.007 mole) of cis, trans-3-(2-bromo-3,3,3-trifluoro-1-propenyl)-2,2-dimethylcyclopropanecarboxylic acid (compound 4.1, Table III), 1.7 g (0.007 mole) of 3-bromomethyl[1,1'-biphenyl], 0.6 g (0.008 mole) of potassium hydroxide, and 0.1 g of 1,4-diazabicyclo[2.2.2]octane in 20 ml of heptane and 20 ml of acetonitrile.

The crude product was purified by column chromatography on silica gel, eluting with 5% toluene in hexane, 10% toluene in hexane, and finally 20% toluene in hexane. The appropriate fractions were combined to give 0.2 g of [1,1'-biphenyl]-3-ylmethyl trans-3-(2-bromo-3,3,3-trifluoro-1-propenyl)-2,2-dimethylcyclopropanecarboxylate. The nmr and ir spectra were consistent with the proposed structure.

Analysis calc'd for $C_{22}H_{20}BrF_3O_2$: C 58.29; H 4.45; Found: C 58.41; H 4.40.

EXAMPLE 19

SYNTHESIS OF (2,4-DICHLORO[1,1'-BIPHENYL]-3-YL)METHYL CIS-3-(2,3-DICHLORO-3,3-DIFLUORO-1-PROPENYL)-2,2-DIMETHYLCYCLO-PROPANECARBOXYLATE

A. Preparation of 2,4-dichloro-3-methylaniline as an intermediate.

A stirred solution of 50.0 g (0.243 mole) of 2,6-dichloro-3-nitrotoluene and 225 g (1.0 mole) of stannous chloride in 250 ml of concentrated hydrochloric acid and 125 ml of ethanol was heated under reflux for 1 hour. The reaction mixture was allowed to cool to ambient temperature and was stirred for 16 hours, made basic with sodium hydroxide, and concentrated under reduced pressure. The residue was slurried with water and the insolubles were collected by filtration and allowed to air dry. The solid was digested with 500 ml of chloroform and 100 ml of ethanol. The mixture was filtered and the filtrate concentrated under reduced pressure to give 33.5 g of 2,4-dichloro-3-methylaniline, m.p. 56°–57.5° C. The nmr spectrum was consistent with the proposed structure.

B. Preparation of 2,4-dichloro-3-methylacetanilide as an intermediate.

A stirred solution of 36.6 g (0.208 mole) of 2,4-dichloro-3-methylaniline in 30 ml of acetic anhydride and 30 ml of acetic acid was heated under reflux for 40 minutes. The reaction mixture was cooled and poured into 250 ml of cold water, and the mixture extracted with three 100 ml portions of chloroform. The combined extracts were washed with three 400 ml portions of a saturated aqueous solution of sodium chloride, dried with magnesium sulfate, filtered, and the filtrate concentrated under reduced pressure to give a solid residue. The solid was recrystallized from toluene-hexane to give 42.9 g of 2,4-dichloro-3-methylacetanilide; m.p. 118°–118.5° C. The nmr spectrum was consistent with the proposed structure.

C. Preparation of 2,4-dichloro-3-methyl[1,1'-biphenyl] as an intermediate.

Nitrosylsulfuric acid (11.6 g) was cautiously added portionwise during 15 minutes to a stirred and refluxing solution of 20.0 g (0.092 mole) of 2,4-dichloro-3-methylacetanilide and 22.0 g (0.28 mole) of anhydrous sodium acetate in 1000 ml of benzene, causing a vigorous reaction. Upon complete addition refluxing was continued for an additional 0.5 hour, then a second portion (11.6 g, 0.183 mole total) of nitrosylsulfuric acid was added portionwise during 15 minutes and refluxing was continued for an additional 1 hour. During a 0.5 hour cooling period the rapidly stirred reaction mixture was flushed with nitrogen. The reaction mixture was washed with one portion of 800 ml of water, one portion of 300 ml of a saturated aqueous solution of sodium bicarbonate and, finally, with one portion of a saturated aqueous solution of sodium chloride. The organic layer was dried with magnesium sulfate, filtered and the filtrate concentrated under reduced pressure to give a dark residual oil. The residual oil was distilled under reduced pressure using a Kugelrohr bulb to bulb distilling system to give a red oil, b.p. 130° C./0.05 mm. The oil was further purified by column chromatography on silica gel using hexane as the eluant. The appropriate fractions were combined and concentrated under reduced pressure to give 10.6 g of 2,4-dichloro-3-methyl[1,1'-biphenyl]. The nmr spectrum was consistent with the proposed structure.

D. Preparation of 3-bromomethyl-2,4-dichloro-[1,1'-biphenyl] as an intermediate.

A stirred solution of 10.6 g (0.045 mole) of 2,4-dichloro-3-methyl[1,1'-biphenyl] and 8.0 g (0.045 mole) of N-bromosuccinimide in 100 ml of carbon tetrachloride was irradiated with a 250 watt infra-red lamp for 4 hours. The reaction mixture was allowed to reflux from the heat of the lamp during the 4 hour period. The reaction mixture was filtered and the filter cake was washed with one portion of 100 ml of carbon tetrachloride. The wash and filtrate were combined and washed with one portion of a saturated aqueous solution of sodium chloride. The organic layer was dried with magnesium sulfate, filtered and the filtrate concentrated under reduced pressure to give 14.1 g of 3-bromomethyl-2,4-dichloro[1,1'-biphenyl]. The nmr spectrum was consistent with the proposed structure.

E. Synthesis of (2,4-dichloro[1,1'-biphenyl]-3-yl)methyl cis-3-(2,3-dichloro-3,3-difluoro-1-propenyl)-2,2-dimethylcyclopropanecarboxylate.

This compound was prepared in the manner of Examples 8, 9, and 10 using 2.3 g (0.009 mole) of cis, trans-3-(2,3-dichloro-3,3-difluoro-1-propenyl)-2,2-dimethylcyclopropanecarboxylic acid (compound 4.4, Table III), 0.6 g (0.009 mole) of potassium hydroxide, 2.8 g (0.009 mole) of 3-bromomethyl-2,4-dichloro[1,1'-biphenyl] and 0.1 g of 1,4-diazabicyclo[2.2.2]octane in 50 ml of heptane and 50 ml of acetonitrile. The crude product was purified by removing the volatiles by distillation using a Kugelrohr bulb to bulb distilling system at 130°–140° C./0.3–0.5 mm. The pot residue was subjected to column chromatography on silica gel, eluting with hexane, then 25:1-hexane:ethyl acetate. Appropriate fractions were combined and subjected to liquid chromatography using 66.6:1-hexane:ethyl acetate as the eluant. The appropriate fractions were combined to give 0.29 g of (2,4-dichloro[1,1'-biphenyl]-3-yl)methyl cis-3-(2,3-dichloro-3,3-difluoro-1-propenyl)-2,2-dimethylcyclopropanecarboxylate. The nmr and ir spectra were consistent with the proposed structure.

Analysis calc'd for $C_{22}H_{18}Cl_4F_2O_2$: C 53.47; H 3.67; Found: C 53.52; H 3.68.

EXAMPLE 20

SYNTHESIS OF (2-METHYL[1,1'-BIPHENYL]-3-YL)METHYL CIS-3-(2-CHLORO-3,3,3-TRIFLUORO-1-PROPENYL)-2,2-DIMETHYLCYCLOPROPANECARBOXYLATE

A. Preparation of 3-hydroxymethyl-2-methylaniline hydrochloride as an intermediate.

Concentrated hydrochloric acid (5.2 ml) was slowly added to a stirred and refluxing mixture of 41.8 g (0.25 mole) of 2-methyl-3-nitrophenylmethanol, 85.0 g of iron powder, and 100 ml of 50% aqueous ethanol. Refluxing and stirring was continued for 2 hours, then the mixture was made just basic by the addition of a 15% ethanolic solution of potassium hydroxide. The hot mixture was filtered through diatomaceous earth, and the filter cake was washed with ethanol. The ethanol washings were combined with the filtrate, and the whole was made acidic with hydrogen chloride and allowed to stand for 16 hours. The solution was concentrated under reduced pressure to give a residue. Hexane was added and the water-hexane azeotrope was removed by distillation. The azeotropic distillation was repeated twice to give an undetermined amount of 3-hydroxymethyl-2-methylaniline hydrochloride, which was used in the next reaction in this sequence without further characterization.

B. Preparation of (3-iodo-2-methylphenyl)methanol as an intermediate.

A stirred solution of 3-hydroxymethyl-2-methylaniline hydrochloride from step A above and 17.2 ml of concentrated sulfuric acid in ice-water was cooled to 0° C., and a solution of 17.3 g (0.25 mole) of sodium nitrite in water was added dropwise. Upon complete addition the reaction mixture was stirred for an additional 0.5 hour, then an additional 8 ml of concentrated sulfuric acid was added dropwise. With the reaction mixture temperature still being maintained at 0° C., a solution of 49.8 g (0.30 mole) of potassium iodide in water was added dropwise, followed by the addition of 0.1 g of copper powder. The cooling bath was removed and the reaction mixture was slowly warmed to 70° C. After 1 hour at 70° C. the reaction mixture was allowed to cool to ambient temperature and stand for 18 hours. Water was added and the mixture was extracted with chloroform. The chloroform extract was washed with a saturated aqueous solution of sodium bisulfite, then with water. The chloroform layer was dried, filtered, and the filtrate concentrated under reduced pressure to give 15.2 g of (3-iodo-2-methylphenyl)-methanol as a dark solid. The nmr and ir spectra were consistent with the proposed structure.

C. Preparation of 2-methyl[1,1'-biphenyl]-3-methanol as an intermediate.

To 5.0 g (0.02 mole) of (3-iodo-2-methylphenyl)methanol and 800 ml of benzene in a photoreactor was added 5.0 g (0.04 mole) of sodium thiosulfate in 15 ml of water. The mixture was purged with argon for 30 minutes then irradiated with a 200 watt medium pressure ultraviolet lamp. The reaction was monitored by gas chromatography. After 36.5 hours the reaction mixture was transferred to a 2000 ml separatory funnel. The photoreactor was rinsed with approximately 20 ml each of water, chloroform, and acetone and the rinsings were added to the separatory funnel. The aqueous layer was separated, and the organic layer was washed with aqueous 0.5 M sodium thiosulfate, then with a saturated aqueous solution of sodium chloride. The organic layer was dried, filtered, and the filtrate concentrated under reduced pressure to give 4.3 g of an oil residue. Gas chromatographic analysis of the oil indicated it to consist of 64% starting material and 36% product. The oil was subjected to column chromatography on silica gel, eluting with 1:1 hexane:chloroform, to give 2.4 g of 2-methyl-[1,1'-biphenyl]-3-methanol. The nmr and ir spectra were consistent with the proposed structure.

D. Synthesis of (2-methyl[1,1'-biphenyl]-3-yl)methyl cis-3-(2-chloro-3,3,3-trifluoro-1-propenyl)-2,2-dimethylcyclopropanecarboxylate.

This compound was prepared in the manner of Example 13, using 1.7 g (0.007 mole) of cis-3-(2-chloro-3,3,3-trifluoro-1-propenyl)-2,2-dimethylcyclopropanecarbonyl chloride, 1.7 g (0.007 mole) of 2-methyl[1,1'- biphenyl]-3-methanol, and 0.55 ml (0.007 mole) of pyridine in 40 ml of toluene.

The crude product was purified by preparative gas chromatography to give 0.15 g of (2-methyl[1,1'-biphenyl]-3-yl)methyl cis-3-(2-chloro-3,3,3-trifluoro-1-propenyl)-2,2-dimethylcyclopropanecarboxylate. The nmr and ir spectra were consistent with the proposed structure.

EXAMPLE 21

SYNTHESIS OF (2,4-DIFLUORO[1,1'-BIPHENYL]-3-YL)METHYL CIS-3-(2-CHLORO-3,3,3-TRIFLUORO-1-PROPENYL)-2,2-DIMETHYLCYCLO-PROPANECARBOXYLATE

A. Preparation of (2,6-difluorophenyl)methanol as an intermediate.

A stirred solution of 25.0 g (0.158 mole) of 2,6-difluorobenzoic acid in 300 ml of diethyl ether was purged with nitrogen, and 20 ml of a 1 molar solution of borane in tetrahydrofuran was carefully added dropwise. The addition caused the reaction mixture to effervesce. When vigorous effervescence subsided, the reaction mixture was heated to reflux and an additional 170 ml of a 1 molar solution of borane (0.190 mole total) in tetrahydrofuran was added dropwise at a rate just sufficient to promote gentle reflux. Upon complete addition the reaction mixture was heated under reflux for an additional 1 hour, allowed to cool to ambient temperature and stand for 16 hours, then heated under reflux again for 1 hour. Acetic acid (11 ml, 0.19 mole) was added, then the reaction mixture was cooled in an ice-water bath and 100 ml of a saturated aqueous solution of ammonium chloride was added slowly. Upon complete addition the reaction mixture was stirred for 0.5 hour, then concentrated under reduced pressure to give a pasty residue. Diethyl ether was added and the mixture was washed with three portions of water, two portions of aqueous 10% sodium carbonate, two portions of water, and one portion of a saturated aqueous solution of sodium chloride. The organic layer was dried with magnesium sulfate, filtered, and the filtrate concentrated under reduced pressure to give 18.9 g of (2,6-difluorophenyl)methanol as a yellow oil. The nmr spectrum was consistent with the proposed structure.

B. Preparation of (2,6-difluorophenyl)methyl acetate as an intermediate.

Pyridine (9.8 g, 0.133 mole) was added to a stirred solution of 18.9 g (0.130 mole) of (2,6-difluorophenyl)methanol in 250 ml of toluene. The resultant solution was heated to reflux while 10.4 g (0.133 mole) of acetyl chloride was added portionwise. Upon complete addition the reaction mixture was heated under reflux for an additional 3 hours, then cooled and washed with three portions of water, two portions of aqueous 2% hydrochloric acid, two portions of water, two portions of aqueous 10% sodium carbonate, two portions of water, and finally, one portion of a saturated aqueous solution of sodium chloride. The organic layer was dried with magnesium sulfate, filtered and the filtrate concentrated under reduced pressure to give a residual oil. The oil was distilled at 36°-53° C./0.10-0.18 mm. Gas chromatographic analysis of the distillates indicated the presence of the starting (2,6-difluorophenyl)methanol. The distillates were combined and heated under reflux for 16 hours with 1.7 g (0.015 mole) of acetyl chloride and 1.1 g of pyridine (0.015 mole) in toluene to give, after work up as described above, 16.8 g of (2,6-difluorophenyl)methyl acetate as a yellow oil. The nmr spectrum was consistent with the proposed structure.

C. Preparation of (2,6-difluoro-3-iodophenyl)-methyl acetate as an intermediate.

Thallium tris(trifluoroacetate) (24.5 g, 0.045 mole) was added to a stirred solution of 16.8 g (0.090 mole) of (2,6-difluorophenyl)methyl acetate in 60 ml of trifluoroacetic acid. The reaction mixture was heated at 40°-50° C. for 15 minutes then 12.7 g (0.05 mole) of iodine was added. Upon complete addition the reaction mixture was heated under reflux for an additional 2 hours. The solvent was removed under reduced pressure and replaced with an equal volume of methylene chloride. The methylene chloride was removed under reduced pressure to give an oily residue. The residue was poured onto ice, using water and diethyl ether to rinse. The mixture was stirred for 30 minutes as 10 g of sodium metabisulfite and then 40 ml of a 5% aqueous solution of sodium hydroxide were added. The aqueous phase was separated and the organic phase was washed with two portions of water, one portion of a 5% aqueous solution of sodium thiosulfate, two portions of water, and finally one portion of a saturated aqueous solution of sodium chloride. The organic layer was dried with magnesium sulfate, filtered, and the filtrate concentrated under reduced pressure to give a residual oil. The oil was distilled under reduced pressure to give 10.5 g of (2,6-difluoro-3-iodophenyl)methyl acetate, b.p. 70°-80° C./2.2 mm. The nmr spectrum was consistent with the proposed structure.

D. Preparation of (2,4-difluoro[1,1'-biphenyl]-3-yl)methyl acetate as an intermediate.

A solution of 4.5 g (0.14 mole) of (2,6-difluoro-3-iodophenyl)methyl acetate in benzene and a solution of 4.5 g of sodium thiosulfate in 15 ml of water were placed in a photoreactor containing a quartz immersion cell. The reaction mixture was irradiated with a 200 watt medium pressure mercury vapor lamp. The system was purged with nitrogen during the course of the reaction. After 6.25 hours of irradiation, the reaction, which was monitored by gas chromatography and had progressed to 88% completion, was terminated.

The reaction mixture was washed with one portion of aqueous 0.5 molar sodium thiosulfate, one portion of water, and finally one portion of a saturated aqueous solution of sodium chloride. The organic layer was dried with magnesium sulfate, filtered, and the filtrate concentrated under reduced pressure to give 3.8 g of a residual oil. An additional 1.8 g of oil from a previous run of the same reaction was combined with the 3.8 g, and the total subjected to column chromatography on silica gel. Elution was accomplished with hexane, 10% methylene chloride-hexane, 20% methylene chloride-hexane, 30% methylene chloride-hexane, 60% methylene chloride-hexane, 80% methylene chloride-hexane, and finally 100% methylene chloride. The appropriate fractions were combined and concentrated under reduced pressure to give 3.1 g of (2,4-difluoro[1,1'-biphenyl]-3-yl)methyl acetate. The nmr spectrum was consistent with the proposed structure.

E. Preparation of 2,4-difluoro[1,1'-biphenyl]-3-methanol as an intermediate.

A solution of 3.1 g (0.012 mole) of (2,4-difluoro[1,1'-biphenyl]-3-yl)methyl acetate in 25 ml of a 2% aqueous solution of sodium hydroxide and 75 ml of methanol was stirred at ambient temperature until the reaction was complete as indicated by thin layer chromatography. The reaction mixture was neutralized with glacial acetic acid and concentrated under reduced pressure to give a residual solid. The solid was partitioned between diethyl ether and water. The phases were separated and the aqueous phase was extracted with two portions of diethyl ether. The ether layers were combined and washed with one portion of 150 ml of 2% aqueous hydrochloric acid, one portion of 150 ml of water, one portion of 150 ml of a 10% aqueous solution of sodium carbonate, one portion of 150 ml of water, and finally, one portion of a saturated aqueous solution of sodium chloride. The organic layer was dried with magnesium sulfate, filtered, and the filtrate concentrated under reduced pressure to give 2.3 g of 2,4-difluoro[1,1'-biphenyl]-3-methanol. The nmr spectrum was consistent with the proposed structure.

F. Synthesis of (2,4-difluoro[1,1'-biphenyl]-3-yl)methyl cis-3-(2-chloro-3,3,3-trifluoro-1-propenyl)-2,2-dimethylcyclopropanecarboxylate.

A stirred solution of 2.6 g (0.011 mole) of cis-3-(2-chloro-3,3,3-trifluoropropenyl)-2,2-dimethylcyclopropanecarboxylic acid in 40 ml of dry toluene was heated to gentle reflux. To this solution, under a nitrogen atmosphere, was added 1.2 ml (0.011 mole) of oxalyl chloride by syringe. Upon complete addition the reaction mixture heated at reflux for an additional 10 minutes, then cooled.

The solution above was added dropwise during 30 minutes to a stirred solution of 2.3 g (0.010 mole) of 2,4-difluoro[1,1'-biphenyl]-3-methanol and 1.7 g (0.022 mole) of pyridine in 60 ml of toluene. Upon complete addition the reaction mixture was heated under reflux for 45 minutes. The reaction mixture was cooled then partitioned between diethyl ether and water. The aqueous phase was extracted with diethyl ether. The combined organic layers were washed with one portion of 150 ml of water, two portions of 150 ml each of a 10% aqueous solution of sodium carbonate, one portion of 150 ml of water, and finally, one portion of 150 ml of a saturated aqueous solution of sodium chloride. The organic layer was dried with magnesium sulfate, filtered, and the filtrate concentrated under reduced pressure to give a residual oil. The oil was purified by column chromatography on silica gel eluting with 20% methylene chloride-hexane, then 40% methylene chloride-hexane. The appropriate fractions were combined to give 2.7 g of (2,4-difluoro[1,1'-biphenyl]-3-yl)methyl cis-3-(2-chloro-3,3,3-trifluoro-1-propenyl)-2,2-dimethylcyclopropanecarboxylate. The nmr spectrum was consistent with the proposed structure.

Analysis calc'd for $C_{22}H_{18}ClF_5O_2$: C 59.43, H 4.05; Found: C 59.92, H 4.01.

EXAMPLE 22

Synthesis of (2,4-dichloro[1,1'-biphenyl]-3-yl)methyl cis,trans-3-(2-chloro-3,3,3-trifluoro-1-propenyl)-2,2-dimethylcyclopropanecarboxylate This compound was prepared in the manner of Examples 13 and 14, using 0.97 g (0.004 mole) of cis,trans-3-(2-chloro-3,3,3-trifluoro-1-propenyl)-2,2-dimethylcyclopropanecarboxylic acid, 0.63 g (0.008 mole) of pyridine, 0.60 g (0.005 mole) of thionyl chloride and 1.1 g (0.004 mole) of 2,4-dichloro[1,1'-biphenyl]-3-methanol (prepared in the manner of Example 21) in 50 ml of toluene.

The crude reaction product was purified by preparative thin layer chromatography on silica gel. Elution was accomplished with 1:1-diethyl ether:hexane. The yield was 0.18 g of (2,4-dichloro[1,1'-biphenyl]-3-yl)methyl, cis,trans-3-(2-chloro-3,3,3-trifluoro-1-propenyl)-2,2-dimethylcyclopropanecarboxylate.

Analysis calc'd for $C_{22}H_{18}Cl_3F_3O_2$: C 55.30, H 3.79; Found: C 55.21, H 3.62.

EXAMPLE 23

Synthesis of (3'-fluoro[1,1'-biphenyl]-3-yl)methyl cis,trans-3-(2-chloro-3,3,3-trifluoro-1-propenyl)-2,2-dimethylcyclopropanecarboxylate A. Preparation of 1-(3-fluorophenyl)-3-methyl-1-cyclohexanol as an intermediate.

A solution of 50.0 g (0.28 mole) of 3-bromofluorobenzene in 100 ml of diethyl ether was added dropwise with stirring to a cooled reaction vessel containing 7.0 g (0.29 mole) of freshly dried magnesium turnings. The reaction began after 10–20% of the 3-bromofluorobenzene-ether solution had been added. The remainder of the addition was done at a rate sufficient to promote gentle reflux. Upon complete addition an additional 210 ml of diethyl ether was added and the reaction mixture was heated under reflux for 1 hour. The reaction mixture was cooled to 5° C. and 32.5 g (0.29 mole) of 3-methylcyclohexanone in 100 ml of diethyl ether was added dropwise during 30 minutes. Upon complete addition the reaction mixture was stirred for 1 hour at 5° C., heated to reflux temperature for 30 minutes, then allowed to cool to ambient temperature and stand for 16 hours. The reaction mixture was slurried in 450 ml of water and made acidic with aqueous 10% hydrochloric acid. The two phases were separated and the aqueous phase was extracted with three portions of diethyl ether. The combined ether extracts and organic phase were washed with two portions of a saturated aqueous solution of sodium bicarbonate, then one portion of water. The organic layer was dried with sodium sulfate, filtered, and the filtrate concentrated under reduced pressure to give 58.0 g of 1-(3-fluorophenyl)-3-methyl-1-cyclohexanol as a solid. The compound was used without further purification.

B. Preparation of 1-(3-fluorophenyl)-3-methyl-1-cyclohexene as an intermediate.

A stirred solution of 58.0 g (0.28 mole) of 1-(3-fluorophenyl)-3-methyl-1-cyclohexanol and 7.2 g (0.04 mole) of p-toluenesulfonic acid in toluene was heated under reflux for 5.5 hours, then under low heat for 16 hours. Gas chromatographic analysis of the reaction mixture indicated the reaction to be 90% complete. An additional 1.0 g of p-toluenesulfonic acid was added and the reaction mixture was heated to reflux and stirred for 10 hours. GC analysis of the reaction mixture indicated the reaction to be 96% complete. An additional 1.0 g of p-toluenesulfonic acid was added and the heating under reflux was continued for 5 hours. The cooled reaction mixture was washed with one portion of a saturated aqueous solution of sodium bicarbonate, then one portion of water. The organic layer was dried with sodium sulfate, filtered, and the filtrate concentrated under reduced pressure to give 41.7 g of 1-(3-fluorophenyl)-3-methyl-1-cyclohexane as a solid. The solid was used without further purification.

C. Preparation of 3'-fluoro-3-methyl[1,1'-biphenyl] as an intermediate.

A stirred mixture of 40.7 g (0.21 mole) of 1-(3-fluorophenyl)-3-methyl-1-cyclohexane and 15.8 g (0.49 mole) of sulfur was heated at 230°–260° C. for 8 hours. The mixture was cooled to ambient temperature, and 150 ml of diethyl ether was added. The mixture was filtered and the filtrate was concentrated under reduced pressure. The residue was subjected to column chromatography on silica gel, eluting with hexane. The appropriate fractions were combined to give 17.2 g of 3'-fluoro-3-methyl[1,1'-biphenyl].

D. Preparation of 3-bromomethyl-3'-fluoro[1,1'-biphenyl] as an intermediate.

This compound was prepared in the manner of Example 19D, using 5.0 g (0.025 mole) of 3'-fluoro-3-methyl[1,1'-biphenyl] and 4.8 g (0.03 mole) of N-bromosuccimide in 50 ml of carbon tetrachloride. The reaction was repeated several times to give, as combined product, 6.6 g of 3-bromomethyl-3'-fluoro[1,1'-biphenyl].

E. Synthesis of (3'-fluoro[1,1'-biphenyl]-3-yl)methyl cis,trans-3-(2-chloro-3,3,3-trifluoro-1-propenyl)-2,2-dimethylcyclopropanecarboxylate.

This compound was prepared in the manner of Examples 8, 9, and 10 using 8.0 g (0.033 mole) of cis,trans-3-(2-chloro-3,3,3-trifluoro-1-propenyl)-2,2-dimethylcyclopropanecarboxylic acid, 8.6 g (0.032 mole) of 3-bromomethyl-3'-fluoro[1,1'-biphenyl], 2.0 g (0.035 mole) of potassium hydroxide in 18 ml of water, and 0.4 g of 1,4-diazabicyclo[2.2.2]octane in 65 ml of heptane and 65 ml of acetonitrile. The crude product was purified by distillation under reduced pressure to give 6.6 g of (3'-fluoro[1,1'-biphenyl]-3-yl)methyl cis,trans-3-(2-chloro-3,3,3-trifluoro-1-propenyl)-2,2-dimethylcyclopropanecarboxylate. The nmr spectrum was consistent with the proposed structure.

Analysis calc'd for $C_{22}H_{19}ClF_4O_2$: C 61.90, H 4.48; Found: C 60.57, H 4.50.

In the method aspect of this invention an effective insecticidal amount of the compound is applied to the locus where insect control is desired, e.g., to the insect itself or to the foliage or seeds of agricultural plants. The compounds are useful for the control of household, veterinary, and crop insects and may be applied as technical material or as a formulated product. Typical formulations include compositions of the active ingredient in combination with an agriculturally acceptable carrier or extender, preferably with a surface-active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of the active ingredient depending upon the particular agent used, the additives and carriers used, other active ingredients and the desired mode of application. With due consideration of these factors, the active ingredient of a typical formulation may, for example, be suitably present at a concentration of about 0.1% up to about 99.5% by weight of the formulation. an agriculturally acceptable carrier may comprise about 99.5% by weight to as low as about 0.5% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in the use dilution may be in the range of about 0.01 to about 10% by weight.

Many variations of spraying, dusting, and controlled or slow release compositions of a type known in the art may be used by substituting or adding a compound of this invention into the compositions known or apparent to the art.

The compounds of this invention may be formulated and applied with other compatible active agents, including nematicides, insecticides, acaricides, fungicides, plant regulators, herbicides, fertilizers, etc.

In applying these compounds, whether alone or with other agricultural chemicals, an effective insecticidal amount of the active ingredient must be applied. While the application rate will vary widely depending on the choice of compound, the formulation and mode of application, the plant species being protected, and the planting density, a suitable use rate may be in the range of 0.005 to 3 kg./hectare, preferably 0.01 to about 1 kg./hectare.

The compounds of this invention were tested for insecticidal activity as described below.

EXAMPLE 24

Initial Contact Activity

The test compound was dissolved in a small amount of acetone, and the acetone solution was dispersed in water containing one drop of isooctylphenyl polyethoxyethanol to make a solution having 1250 ppm (w/w) or 512 ppm (w/w) active ingredient. Aliquots of this solution were diluted with an appropriate amount of water to provide solutions containing various concentrations of active ingredient. Test organisms and techniques were as follows: the activity against Mexican bean beetle (*Epilachna varivestis* Muls.) and southern armyworm (*Spodoptera eridania* [Cram.]) was evaluated by dipping the leaves of pinto bean plants into the test solution or spraying with the test solution and infesting the leaves with the appropriate immature-form insects after the foliage had dried. The activity against the pea aphid (*Acyrthosiphon pisum* [Harris]) was evaluated on broad bean plants whose leaves were dipped or sprayed before infestation with adult aphids. The activity against twospotted spider mites (*Tetranychus urticae* [Koch]) was evaluated on pinto bean plants whose leaves were dipped or sprayed with test solution after infestation with adult mites. The activity against the milkweed bug (*Oncopeltus faciatus* [Dallas]) and the plum curculio (*Conatrachelus nenuphar* [Herbst]) was evaluated by spraying the test solutions into glass dishes or jars containing the adult insects. Following application of the compound and infestation the tests were maintained in a holding room at 20° C. and 50% relative humidity for an exposure period of at least 48 hours. At the end of this time the dead and living insects or mites were counted, and the percent kill was calculated. Results of these tests are summarized in Table V. In general, the compounds of the invention exhibited excellent insecticidal activity on these tests.

EXAMPLE 25

Comparative Testing, DV and TFP Compounds

Various trifluoropropenyl (TFP) componds of the invention, i.e., compounds in which one of Y and Z is trifluoromethyl, were compared for insecticidal activity with the corresponding dichlorovinyl (DV) compound

[1,1'-biphenyl]-3-ylmethyl cis-3-(2,2-dichlorovinyl)-2,2-dimethylcyclopropanecarboxylate of U.S. Pat. No. 4,130,657.

A topical application procedure was employed for the insect species southern armyworm (*Spodoptera eridania* [Cram.]), beet armyworm (*Spodoptera exigua* [Hubner]), corn earworm (*Heliothis zea* [Boddie]), tobacco budworm (*Heliothis virescens* [Fabricius]), cabbage looper (*Trichoplusia ni* [Hubner]), Mexican bean beetle (*Epilachna varivestus* Muls.), and milkweed bug (*Oncopeltus faciatus* [Dallas]). In this test appropriate amounts of a solution containing 5 mg/l of test compound in acetone were applied to the insect. The tests were read twenty-four hours after application of the test solution and the percent kill determined.

The foliar application procedure described in Example 24 above was employed for the insect species pea aphid (*Acyrthosiphon pisum* [Harris]).

Relative potency, based on a value of 1.0 for the DV compound, was determined by comparing percent kill for the TFP compounds of the invention with the percent kill for the DV compound. The results of these tests are shown in Table VI below. The insect species above are respectively identified in the table by the abbreviations, SAW, BAW, CEW, TBW, CL, MBB, MWB, and PA. The compounds of the invention in general were about 2 to 4 times as active as the DV compound.

TABLE I

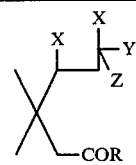

| Example | X | Y | Z | R |
|---|---|---|---|---|
| 1.1[a] | Br | CF$_3$ | Br | OCH$_3$ |
| 1.2[a] | Cl | CF$_3$ | F | OCH$_3$ |
| 1.3[a] | Cl | CF$_3$ | H | OCH$_3$ |
| 1.4[a] | Cl | CF$_2$Cl | Cl | OCH$_3$ |
| 1.5[a] | Cl | CF$_2$Cl | F | OCH$_3$ |
| 1.6[a] | Cl | CFCl$_2$ | F | OCH$_3$ |
| 1.7[a] | Cl | CF$_2$CF$_2$Cl | Cl | OCH$_3$ |
| 1.8[b] | Cl | C$_2$F$_5$ | Cl | OCH$_3$ |

[a]Boiling points (°C./mmHg): 1.1:63/0.08; 1.2:71/0.09; 1.3:112–115°/7; 1.4:95–106/0.1–0.125; 1.5:58–60/0.005; 1.6:103/0.2–0.3; 98–102/0.05.
[b]Structure confirmed by nmr.

TABLE II

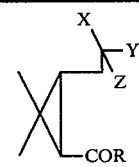

| Example | X | Y | Z | R |
|---|---|---|---|---|
| 2.1[a] | Br | CF$_3$ | Br | OCH$_3$ |
| 2.2 | Cl | CF$_3$ | F | OCH$_3$ |
| 2.3[b] | Cl | CF$_3$ | H | OCH$_3$ |
| 2.4 | Cl | CF$_2$Cl | Cl | OCH$_3$ |
| 2.5[a] | Cl | CF$_2$Cl | F | OCH$_3$ |
| 2.6 | Cl | CFCl$_2$ | F | OCH$_3$ |
| 2.7[b] | Cl | CF$_2$CF$_2$Cl | Cl | OCH$_3$ |

[a]Boiling points: (°C./mm Hg): 2.1:100–113°/0.09–0.1; 2.5:45–47°/0.02
[b]Structure confirmed by nmr

TABLE III

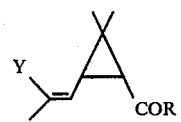

| Example | Y | Z | R | Isomer |
|---|---|---|---|---|
| 3.1[b] | CF$_3$ | Br | OCH$_3$ | c/t |
| 3.2[b] | CF$_3$ | F | OCH$_3$ | c/t |
| 3.3 | CF$_3$ | H | OCH$_3$ | c/t |
| 3.4[b] | CF$_2$Cl | Cl | OCH$_3$ | c/t |
| 3.5[b] | CF$_2$Cl | F | OCH$_3$ | c/t |
| 3.6[b] | CFCl$_2$ | F | OCH$_3$ | c/t |
| 3.7[b] | CF$_2$CF$_2$Cl | Cl | OCH$_3$ | c/t |
| 3.8[b] | C$_2$F$_5$ | Cl | OCH$_3$ | c/t |
| 4.1[c] | CF$_3$ | Br | OH | c/t |
| 4.2[d] | CF$_3$ | F | OH | c/t |
| 4.3[a] | CF$_3$ | H | OH | c/t |
| 4.4[a] | CF$_2$Cl | Cl | OH | c/t |
| 4.5[c] | CF$_2$Cl | F | OH | c |
| 4.6[c] | CF$_2$CF$_2$Cl | Cl | OH | c/t |
| 4.7 | C$_2$F$_5$ | Cl | OH | c/t |
| 4.8[g] | CF$_2$Cl | F | OH | c/t |
| 6.1[e] | CF$_3$ | Br | Cl | c/t |
| 6.2[e] | CF$_3$ | F | Cl | c/t |
| 6.3[f] | CF$_3$ | H | Cl | c/t |
| 6.4[e] | CF$_2$Cl | Cl | Cl | c/t |
| 6.5[d,e] | CF$_2$Cl | F | Cl | c |
| 6.6[d,e] | CF$_2$CF$_2$Cl | Cl | Cl | c/t |
| 6.7[b] | C$_2$F$_5$ | Cl | Cl | c/t |
| 6.8[d,e] | CF$_3$ | Cl | Cl | c/t |

[a]NMR spectrum consistent with assigned structure.
[b]Boiling points (°C./mm Hg):3.1:44–47°/0.07–0.08; 3.2:71°/29; 3.4:84–88°/1.25–1.4; 3.5:90–92°/11; 3.6:60–71°/0.08; 3.7:59–65°/0.07; 3.9:98–110°/7; 6.7:42–51°/0.1;
[c]Melting points (°C.):4.1:110–116°; 4.5:80–87°; 4.6:67–69°
[d]Structure confirmed by IR spectra
[e]Liquid, not isolated
[f]Semi-solid, not isolated
[g]VPC analysis shows mixture of cis and trans isomers

TABLE IV

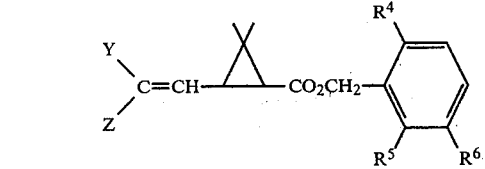

| Compound of Example | Isomer | Y | Z | R$^4$ | R$^5$ | R$^6$ |
|---|---|---|---|---|---|---|
| 8 | cis | CF$_3$ | Cl | H | H | C$_6$H$_5$ |
| 9 | cis | C$_2$F$_5$ | Cl | H | H | C$_6$H$_5$ |
| 10 | cis/trans | C$_2$F$_5$ | Cl | H | H | C$_6$H$_5$ |
| 10 | trans | C$_2$F$_5$ | Cl | H | H | C$_6$H$_5$ |
| 11 | cis | CF$_2$Cl | F | H | H | C$_6$H$_5$ |
| 11 | trans | CF$_2$Cl | F | H | H | C$_6$H$_5$ |
| 12 | cis | CF$_2$Cl | Cl | H | H | C$_6$H$_5$ |
| 12 | trans | CF$_2$Cl | Cl | H | H | C$_6$H$_5$ |
| 13 | cis | CF$_3$ | Br | H | H | C$_6$H$_5$ |
| 14 | cis/trans | CF$_3$ | Br | H | H | C$_6$H$_5$ |
| 15 | cis/trans | CF$_2$CF$_2$Cl | Cl | H | H | C$_6$H$_5$ |
| 15 | cis | CF$_2$CF$_2$Cl | Cl | H | H | C$_6$H$_5$ |
| 16 | cis | CF$_3$ | H | H | H | C$_6$H$_5$ |
| 16 | cis/trans | CF$_3$ | H | H | H | C$_6$H$_5$ |
| 17 | cis | CF$_3$ | F | H | H | C$_6$H$_5$ |
| 17 | trans | CF$_3$ | F | H | H | C$_6$H$_5$ |
| 18 | trans | CF$_3$ | Br | H | H | C$_6$H$_5$ |
| 19 | cis | CF$_2$Cl | Cl | Cl | Cl | C$_6$H$_5$ |
| 20 | cis | CF$_3$ | Cl | H | CH$_3$ | C$_6$H$_5$ |
| 21 | cis | CF$_3$ | Cl | F | F | C$_6$H$_5$ |
| 22 | cis/trans | CF$_3$ | Cl | Cl | Cl | C$_6$H$_5$ |
| 23 | cis/trans | CF$_3$ | Cl | H | H | m-FC$_6$H$_4$ |

TABLE V

Initial Activity

| Comp.[a] of Ex. | Isomer | Conc.[b] | MWB[1] | MBB[2] | SAW[3] | PA[4] | SM[5] | PC[6] |
|---|---|---|---|---|---|---|---|---|
| 8 | C | 20(39)[c] | 10 | 100 | 100 | 100 | (50) | (10) |
| 9 | C | 78 | 25 | 100 | 100 | 100 | 80 | 0 |
| 11 | C | 78 | 95 | 100 | 100 | 100 | 94 | 25 |
| 11 | T | 78 | 90 | 100 | 100 | 100 | 14 | 0 |
| 13 | C | 64 | — | 100 | 100 | 100 | 0 | — |
| 15 | C | 78(312) | 10 | 100 | 100 | 90 | 58 | (0) |
| 16 | C | 78 | 55 | 100 | 100 | 90 | 92 | 0 |
| 17 | C | 78 | 41 | 100 | 100 | 100 | 100 | 55 |
| 18 | T | 64(512) | — | 95 | 100 | 71 | (0) | — |
| 19 | C | 500 | — | — | — | 100 | 100 | — |
| 21 | C | 64 | — | 100 | 100 | 100 | 0 | — |
| 23 | C/T | 32(64) | — | 95 | 100 | 95 | (0) | — |

[a] structure in Table IV
[b] concentration in parts per million
[c] data in parenthesis taken at concentration shown in parenthesis
[1] Milkweed bug
[2] Mexican bean beetle
[3] Southern armyworm
[4] Pea aphid
[5] Two-spotted spider mite
[6] Plum curculio

TABLE VI

Relative Potency[a] of TFP Compounds

| Test Species[b] | Compound of Example[c] | | |
|---|---|---|---|
| | 8 | 13 | 17 |
| SAW | 1.3 | 2.3 | 1.1 |
| BAW | 2.3 | 4.0 | — |
| CEW | 4.0 | 5.5 | — |
| TBW | 2.8 | 4.5 | — |
| CL | 4.0 | 8.5 | 2.5 |
| MBB | 0.6 | 1.3 | — |
| MWB | 2.8 | 5.1 | — |
| PA[d] | 2.7 | 1.1 | — |
| Average | 2.6 | 4.0 | 1.8 |

[a] Based on a value of 1.0 for [1,1'-biphenyl]-3-yl-methyl cis-3-(2,2-dichloroethenyl)-2,2-dimethyl-cyclopropanecarboxylate.
[b] Abbreviations explained in Example 25.
[c] Cis isomer.
[d] Foliar test results; all other data obtained by topical test procedures.

I claim:

1. A compound of the formula

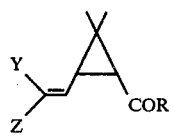

wherein one of Y and Z is a perhaloalkyl group having 1 to 4 carbon atoms and the other is hydrogen, halogen, or lower alkyl; and R is —OR$^1$ where R$^1$ is a group of the formula

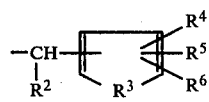

in which R$^2$ is hydrogen, R$^3$ is vinylene; R$^4$ and R$^5$ are independently hydrogen, lower alkyl, halogen, or haloalkyl; and R$^6$ is phenyl which may be substituted with one to three substituents selected from halogen and lower alkyl.

2. The compound of claim 1 in which one of Y and Z is perhaloalkyl of 1 or 2 carbon atoms, the other is halogen; and R$^4$ and R$^5$ are independently hydrogen, lower alkyl or halogen.

3. The compound of claim 2 in which one of Y and Z is trifluoromethyl, the other is halogen, and R$^1$ is a group of the formula

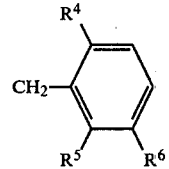

4. The compound of claim 3 in which R$^4$ and R$^5$ are each hydrogen, and R$^6$ is phenyl.

5. The compound of claim 3 in which R$^4$ and R$^5$ are each hydrogen and R$^6$ is 3-fluorophenyl.

6. The compound of claim 3 in which R$^4$ and R$^5$ are each fluorine and R$^6$ is phenyl.

7. The compound of claim 3 in which R$^4$ and R$^5$ are each chlorine and R$^6$ is phenyl.

8. The compound of claim 3 in which R$^4$ is hydrogen, R$^5$ is methyl, and R$^6$ is phenyl.

9. The compound of claim 1, 2, 3, 4, 5, 6, 7 or 8 in which the vinyl and carboxy groups at positions 1 and 3 of the cyclopropane ring are of cis or trans or cis,trans configuration with respect to each other.

10. An insecticidal composition comprising an insecticidal amount of the compound of claim 1, 2, 3, 4, 5, 6, 7 or 8 in admixture with a compatible agriculturally acceptable carrier.

11. A method for insect control which comprises applying to the situs where control is desired an insecticidally effective amount of the compound of claim 1, 2, 3, 4, 5, 6, 7 or 8.

* * * * *

UNITED STATES PATENT AND TRADEMARK OFFICE
CERTIFICATE OF CORRECTION

PATENT NO. : 4,238,505

DATED : December 9, 1980

INVENTOR(S) : John F. Engel

It is certified that error appears in the above—identified patent and that said Letters Patent is hereby corrected as shown below:

Column 20, line 61, "methyl-1-cyclohexane" should read --methyl-1-cyclohexene--; line 66, "phenyl)-3-methyl-1-cyclohexane" should read --phenyl)-3-methyl-1-cyclohexene--. Column 21, line 59, "by weight of the formulation. an agriculturally accept-" should read --by weight of the formulation. An agriculturally accept- --. Column 22, line 61 "on these tests." should read --in these tests.--; line 65, "componds of the" should read --compounds of the--. Column 23, line 48, "98-102/0.05" should read --1.7:98-102/0.05.--.

Signed and Sealed this

Thirtieth Day of June 1981

[SEAL]

Attest:

RENE D. TEGTMEYER

Attesting Officer   Acting Commissioner of Patents and Trademarks